United States Patent
Auge', II

(10) Patent No.: US 6,547,794 B2
(45) Date of Patent: Apr. 15, 2003

(54) METHOD FOR FUSING BONE DURING ENDOSCOPY PROCEDURES

(76) Inventor: Wayne K. Auge', II, 936 Vista Jemez Ct., Santa Fe, NM (US) 87505

( * ) Notice: Subject to any disclaimer, the term of this patent is extended or adjusted under 35 U.S.C. 154(b) by 0 days.

(21) Appl. No.: 09/885,749

(22) Filed: Jun. 19, 2001

(65) Prior Publication Data

US 2002/0022846 A1 Feb. 21, 2002

Related U.S. Application Data

(60) Provisional application No. 60/226,370, filed on Aug. 18, 2000, and provisional application No. 60/272,955, filed on Mar. 2, 2001.

(51) Int. Cl.$^7$ .................................................. A61F 5/00
(52) U.S. Cl. ............................... 606/86; 606/8; 606/60; 606/76; 606/214; 607/51; 424/422
(58) Field of Search ............................. 606/8, 60, 76, 606/86, 214; 128/898; 424/422, 423, 426; 607/51

(56) References Cited

U.S. PATENT DOCUMENTS

| | | | |
|---|---|---|---|
| 3,982,017 A | 9/1976 | Thiele | |
| 4,014,777 A | 3/1977 | Brown | |
| 4,105,017 A | 8/1978 | Ryaby et al. | |
| 4,266,532 A | 5/1981 | Ryaby et al. | |
| 4,266,533 A | 5/1981 | Ryaby et al. | |
| 5,014,699 A | 5/1991 | Pollack et al. | |
| 5,352,463 A | 10/1994 | Badylak et al. | |
| 5,458,596 A | 10/1995 | Lax et al. ...................... | 606/31 |
| 5,494,538 A | 2/1996 | Kirillov et al. | |
| 5,498,259 A | 3/1996 | Mourant et al. | |
| 5,516,533 A | 5/1996 | Badylak et al. | |
| 5,584,863 A | 12/1996 | Rauch et al. | |
| 5,669,904 A | 9/1997 | Platt, Jr. et al. | |
| 5,669,934 A | 9/1997 | Sawyer ........................ | 606/213 |
| 5,683,366 A | 11/1997 | Eggers et al. | |
| 5,697,882 A | 12/1997 | Eggers et al. | |
| 5,741,261 A | 4/1998 | Moskovitz et al. | |
| 5,746,896 A | 5/1998 | Shimamune et al. | |
| 5,749,895 A | 5/1998 | Sawyer et al. ............... | 606/214 |
| 5,788,976 A | 8/1998 | Bradford | |
| 5,824,015 A | 10/1998 | Sawyer ........................ | 606/214 |
| 5,840,166 A | 11/1998 | Kaneko | |
| 5,885,292 A | 3/1999 | Moskovitz et al. | |
| 5,919,191 A | 7/1999 | Lennox et al. | |
| 5,955,514 A | 9/1999 | Huang et al. | |
| 5,964,968 A | 10/1999 | Kaneko | |
| 6,033,654 A | 3/2000 | Stedronsky et al. | |
| 6,135,998 A | 10/2000 | Palanker | |
| 6,149,620 A | 11/2000 | Baker et al. | |
| 6,159,194 A | 12/2000 | Eggers et al. ................ | 604/500 |
| 6,206,878 B1 | 3/2001 | Bishop et al. | |
| 6,213,999 B1 | 4/2001 | Platt, Jr. et al. | |
| 6,241,723 B1 | 6/2001 | Heim et al. | |
| 6,264,652 B1 | 7/2001 | Eggers et al. | |
| 6,322,549 B1 | 11/2001 | Eggers et al. | |

OTHER PUBLICATIONS

Chen, S.S., et al., "Heat–Induced Changes in the Mechanics of a Collagenous Tissue: Isothermal, Isotonic Shrinkage," Transactions of the ASME, vol. 120, pp 382–388 (Jun. 1998).

Fink, B., et al., "Holmium: YAG Laser–Induce Aseptic Bone Necroses of the Femoral Condyle," J of Arthoscopic and Related Surgery, vol. 12, No. 2, pp 217–223 (Apr. 1996).

Ito, T., et al., "Sensitivity of Osteoinductive Activity of Demineralized and Defatted Rat Femur to Temperature and Duration of Heating," Clinical Orthopaedics and Related Research, No. 316, pp 267–275 (Jul. 1995).

Janzen, D.L., et al., Osteonecrosis After Contact Neodymium: Yttrium Aluminum Garnet Arthoscopic Laser Meniscetomy, American Journal of Roentgenol, vol. 169, pp 855–858 (Sep. 1997).

Lopez, M.J., et al., "Effects of Monopolar Radiofrequency Energy on Ovine Joint Capsular Mechanical Properties," Clinical Orthopaedics and Related Research, No. 372, pp 286–297 (May 2000).

Rozbruch, S.R., et al., "Osteonecrosis of the Knee Following Arthroscopic Laser Meniscectomy," J of Arthoscopic and Related Surgery, vol. 12, No. 2, pp 245–250 (Apr. 1996).

Thal, R., et al., "Delayed Articular Cartilage Slough: Two Cases Resulting from Holmium: YAG Laser Damage to Normal Articular Cartilage and a Review of the Literature," J of Arthoscopic and Related Surgery, vol. 12, No. 1, pp 92–94 (Feb. 1996).

Wall, M.S., et al., "Thermal Modification of Collagen," J Shoulder Elbow Surg, pp 339–344 (Jul./Aug. 1999).

Zhang, M., et al., "Effect(s) of the Demineralization Process on the Osteoinductivity of Demineralized Bone Matrix," J. Periodontol, pp 1085–1092 (Nov. 1997).

Wallace, A.L., et al., "Electrothermal Shrinkage Reduces Laxity but Alters Creep Behavior in a Lapine Ligament Model," J. Shoulder Elbow Surg., pp 1–6 (Jan./Feb. 2001).

Mourant, J.R., et al., "Laser Welding of Bone: Successful in vitro Experiments," *Laser Sciences and Applications Group*, Los Alamos NM.

Mourant, J.R., et al., "Improvements in Laser "Welding" of Chicken Bone Tibias in vitro, " Laser Sciences and Applications Group, Los Alamos NM.

*Primary Examiner*—Gregory L. Huson
*Assistant Examiner*—Tuan Nguyen
(74) *Attorney, Agent, or Firm*—Stephen A. Slusher; Jeffrey D. Myers

(57) ABSTRACT

A method of fusing or welding bone in vivo and in a fluid medium, comprising: harvesting a piece of autologous implant bone; treating the implant bone and/or a receiving bone to expose organic component; treating the implant bone and/or the receiving bone by de-fatting; combining the implant bone with other compounds to create an interfacing agent; adding the interfacing agent between receiving bone segments to be fused or welded; and fusing or welding in vivo, in a fluid medium, utilizing electromagnetic energy.

24 Claims, 4 Drawing Sheets

Cancellous-like Structure

Cortical-like Structure

METHOD FOR FUSING BONE DURING ENDOSCOPY PROCEDURES

CROSS-REFERENCE TO RELATED APPLICATIONS

Figure 1:
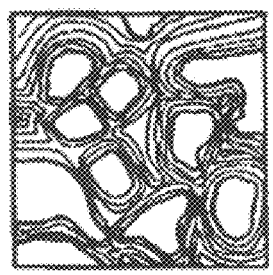
Figure 1:
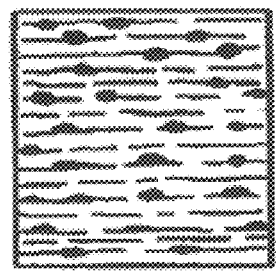

This application claims the benefit of the filing of U.S. Provisional Patent Application Ser. No. 60/226,370, entitled "Method For Fusing Bone During Endoscopy Procedures", filed on Aug. 18, 2000, and of U.S. Provisional Patent Application Ser. No. 60/272,955, entitled "Method For Fusing Bone During Endoscopy Procedures", filed on Mar. 2, 2001, and the specifications thereof are incorporated herein by reference.

BACKGROUND OF THE INVENTION

1. Field of the Invention (Technical Field)

The present invention is directed to the in vivo fusing and/or welding of bone in a fluid medium, particularly useful in endoscopy procedures.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The medical arts do not at present provide a consistent and useful procedure for fusing or welding bone in vivo in a fluid medium, such as during endoscopy procedures. Further, since all in vivo healing and cellular processes occur in a fluid medium and are dependant upon tissue hydration, the prior art does not provide for fusing or welding bone in such fluid circumstances and further where damage to native host tissue is to be avoided.

U.S. Pat. No. 5,498,259, entitled "Method for Fusing Bone" to Mourant, et al. ("Mourant"), is directed to fusing bone by chemically removing the mineral matrix from a thin layer of the surfaces to be joined and then heating the joint using electromagnetic radiation. However, the Mourant process is conducted in vitro, uses a laser, is not conducted in a fluid medium necessary for in vivo or endoscopic use, and does not achieve weld strengths sufficient for in vivo clinical application. Further deficiencies of Mourant are discussed below.

U.S. Pat. Nos. 5,824,015 and 5,749,895 and 5,669,934, to Sawyer, et al., describe joining soft tissues, particularly those with lumens such as arteries, utilizing a surface-applied pre-formed film or sheet of collagen that is treated with electromagnetic energy. The method of union is fundamentally different whereas the substance joining the soft tissue acts like an adhesive tape. This process as disclosed does not apply to hard tissues such as bone, due primarily to the unique structure of bone and to limited weld strengths demonstrated that are insufficient for in vivo use.

U.S. Pat. No. 6,033,654, to Stedronsky, et al., describes joining soft tissue with a proteinaceous recombinant non-biologic polymer adhesive. Tissue apposition is achieved and held during the healing process. The invention is not applicable to bone. The present invention is not directed to an adhesive, but rather a welding process that creates a biologic "grout" construct that interdigitates with cancellous bone providing a mechanical construct for fusion/welding and that does not interfere with healing responses.

U.S. Pat. No. 5,955,514, to Huang, et al., describes a means to join non-biologic implants such as metal and ceramic to biologic materials such as hard tooth material with non-biologic polymer cement. The present invention does not relate to non-biologic implants such as metal or ceramic but rather to fusing normal tissue to normal tissue, rather than fusing bone to metal or ceramic.

U.S. Pat. Nos. 5,885,292 and 5,741,261, to Moskovitz et al., relate to spine surgery rather than endoscopy. Specifically, the means (instrumentation) to achieve a bone fusion is simply providing bone graft to the spine location with specific tools described.

U.S. Pat. No. 5,788,976, to Bradford, relates to spine surgery rather than endoscopy. This is a technique for harvest and preparation of the autologous cancellous bone graft Bradford harvests the graft and separates the constituent elements by centrifuging the material and then uses a portion for treatment. The present invention does not present a bone graft harvest method per se but rather treatment of harvested bone graft. Bradford can make a paste but simply as a delivery method rather than as a means to weld. Bradford simply wants to introduce bone graft to an area, limiting harvest sequelae and allowing the benefits of bone graft to occur at a fusion site. The present invention seeks a structural weld obviating other fixation devices. The autologous graft in the present invention is treated mechanically, chemically, and electromagnetically.

U.S. Pat. No. 5,584,863, to Rauch, et al., U.S. Pat. No. 5,014,699, to Pollack, et al., and U.S. Pat. Nos. 4,266,533, 4,266,532, and 4,105,017, to Ryaby, et al., relate to electrotherapy, a different process than electromagnetic energy or radio frequency delivery to tissue during surgical or electrosurgical procedures.

U.S. Pat. No. 5,458,596, to Lax, et al., U.S. Pat. No. 6,149,620, to Baker, et al., and U.S. Pat. No. 6,159,194, to Eggers, et al, collectively relate to radio frequency or electromagnetic energy delivery to soft-tissue derived collagen rather than bone-derived collagen. Specifically described in these filings are the treatment and/or contraction of "soft tissue", "soft tissue collagen", or "soft tissue derived collagen" by applying radio frequency or electromagnetic energy via a conductive medium. The use of these descriptors in these Patents indicates the distinction between soft tissue-derived and bone-derived collagen further reflecting the non-obvious nature of the present invention utilizing radio frequency or electromagnetic energy during surgical or electrosurgical procedures to treat bone-derived collagen or bone-derived material. Further distinctions are discussed below.

U.S. Pat. No. 3,982,017, to Thiele, relates to specifically designed injectable solutions to aid fracture healing. The present invention utilizes other non-injectable healing aides, such as growth factors, that can be added to the fusing or welding process to augment healing.

U.S. Pat. Nos. 5,516,533 and 5,352,463, to Badylak, et al., relate to soft tissue derived grafts, not bone-derived grafts.

Laser welding of bone as described by Mourant has provided some optimism that the Holy Grail of bone fixation can be achieved, i.e., to obtain normal bone at union sites with no sequelae of fixation devices. In such a scenario, the resultant bone—bone interface would become a normal bone construct after healing. However, results utilizing current techniques as disclosed in prior art have not been successful in attaining these goals, have not been practical in vivo, and, therefore, have not been transferred to clinical application and patient care.

Bone healing occurs via natural processes when mechanical stability and apposition (i.e. compression) are combined with an adequate host healing response. Without both of these mechanical and biologic environments, healing will be impaired. To this end, both components, stability/compression and healing response, can be, and have been, modified, altered, or stimulated by various methods to assist in the host in vivo healing response. Any fusing or welding process should be attentive to both of these fundamental concerns if such processes are to be used clinically or conducted in vivo. Bone fusion or welding has been accomplished in vitro by delivering electromagnetic energy to the bone segments that require fixation after acid treatment. However, the deficiencies of such prior art have obviated use in vivo. The limited bone fusion/welding strength and duration (including decay) that has been achieved (even with application of specific "solders"), the inability to perform fusion/welding in a fluid (in vivo or during endoscopy) environment, and the limited applicability of laser energy to current treatment approaches (regulatory and safety issues, licensing and certification requirements, high equipment costs not amenable to general clinical practice, and issues of collateral damage during tissue application) have reduced the current techniques disclosed in prior art to an in vitro experiment. These techniques do not allow fusion/welding fixation without other supplementary fixation devices and have not been applicable in a fluid and/or in vivo environment.

Provisional fixation techniques are required in orthopedic treatments to hold tissue (bone sections or fragments) in specific positions until adequate, mature healing responses can be developed by the host organism that supercedes the requirement of the provisional fixation initially utilized. Specific to the techniques of the method of fusing bone as stated in Mourant, "after 16–24 hours of immersion in saline solution, however, the union held less than 500 g before failure". This strength, and the decay of this strength in a fluid environment, is not adequate for use in an in vivo environment without additional provisional fixation techniques and more specifically under endoscopy conditions that typically involve a fluid medium. Mourant indicates the need for "external fixation devices applied to stabilize the bone segments". Further, all in vivo healing and cellular processes occur in a fluid medium and are dependent upon tissue hydration (i.e. fluid). These are some of the reasons why the Mourant process has not been applied to clinical practices—it does not obviate the need for other provisional fixation techniques during the entire healing process and therefore the application of the Mourant technique is extraneous, possibly dangerous (e.g. acid treatment to host tissue if used in vivo, collateral damage from laser use such as osteonecrosis, etc.), and economically burdensome. As disclosed, the procedures serve as "an in vitro pre-provisional fixation technique", not "an in vivo provisional fixation technique".

The laser-dye energy direction process as used in Mourant is not amenable in vivo due to the lack of a natural insulator (see disclosure below). Tissue such as articular cartilage, fibrocartilage, bone, and ligament are adjacent to bone segments, particularly as in joints encountered during treatment such as endoscopy procedures, and can be damaged or altered by low level laser energy despite such attempts as dye-solder localization or application mode and technique constraints (B. Fink, et al., "Holmium:YAG laser-induced aseptic bone necrosis of the femoral condyle", *Arthroscopy* 12:217–223 (1996); D. L. Janzen, et al., "Osteonecrosis after contact neodymium:yttrium aluminum garnet arthroscopic laser menisectomy", *American Journal of Roentgenol* 169:855–858 (1997); S. R. Rozbruch, et al., "Osteonecrosis of the knee following arthroscopic laser menisectomy", *Arthroscopy* 12:245–250 (1996); R. Thai, et al., "Delayed articular cartilage slough: two cases resulting from holmium:YAG laser damage to normal articular cartilage and a review of the literature", *Arthroscopy* 12:92–94 (1996)). Limiting collateral damage is critical since it is by the adjacent tissue that the natural host healing responses are generated. Electromagnetic energy induced tissue injury or necrosis impairs both healing responses and the structural integrity of tissue, negatively affecting both of the fundamental components necessary for bone healing. For these reasons, another source of electromagnetic energy delivery is required for bone fusion/welding in vivo.

The prior art for bone fusion/welding has been labeled "an in vitro experiment" since the process is performed outside of the host with the subsequent intentions to re-introduce the segments back into the host for further subsequent and traditional fixation. The process involves acid and electromagnetic energy that is not biocompatible and have raised many concerns regarding iatrogenic damage during such processes if applied clinically. Maintaining structural and cellular integrity during such procedures is critical due to necessary regulatory clearance and acceptance in peer-reviewed medical circles. It is for these reasons, and others to be disclosed below, that prior art does not provide a consistent and useful procedure for fusing or welding bone in vivo in a fluid medium, such as during endoscopy procedures.

SUMMARY OF THE INVENTION
(DISCLOSURE OF THE INVENTION)

The present invention is of a method of fusing or welding bone in vivo and in a fluid medium, comprising: harvesting a piece of autologous implant bone; treating the implant bone and/or a receiving bone to expose organic component; treating the implant bone and/or the receiving bone by de-fatting; combining the implant bone with other compounds to create an interfacing agent; adding the interfacing agent between receiving bone segments to be fused or welded; and fusing or welding in vivo, in a fluid medium, utilizing electromagnetic energy. In the preferred embodiment, the piece of autologous bone and receiving bone segments comprise cancellous bone. In fusing or welding, electromagnetic energy (preferably radio frequency energy) is applied to bone or bone-derived organic tissue to achieve tissue changes. Chemically and/or mechanically treating bone or bone-derived tissue to alter mineral matrix and to de-fat and thereby provide a good fusing or welding surface is desired. Chemically treating may be by treating the bone or bone-derived tissue with acid. Mechanically treating may be by treating the bone or bone-derived tissue to conform it to a shape of another bone. Compressing the bone segments and interfacing agent may occur during fusing or welding, and may cease after fusing or welding is completed. Fusing or welding may be by employing one or both of heating and electromagnetic energy, generated via, for example, lasers and/or radio frequency generators, preferably an electromagnetic instrument probe with broadcast emission capability and scaled reflector geometry of active electrode design to generate radio frequency energy and preferably wherein fusing or welding occurs in an electrically conductive medium. Harvesting and fusing or welding may be repeated with a second piece of bone in a place previously occupied by a temporary provisional fixation device. Prior to fusing or welding, a hydrophobic, lipophilic carrier paste-gel, interfacing agent may be introduced, preferably via impacting the paste-gel interfacing agent complex into porosity of a bone, most preferably into both the implant bone and the receiving bone. The paste-gel operates to direct radio frequency energy into portions of bone to be fused or welded together and additionally operates to insulate against the radio frequency energy portions of bone other than the portions to be fused or welded together. The interfacing agent preferably comprises one or more of osteoconductive, osteoinductive, and osteogenic components designed to augment bone healing, and which are activated, released, or induced by the application of electromagnetic energy. Preferably, a visualization aid such as a dye is deposited.

The invention is further of a fused or welded bone structure prepared by the above method.

The invention is additionally of a method of achieving tissue changes in bone or bone-derived organic tissue comprising providing bone or bone-derived organic tissue and applying electromagnetic energy application to the bone or bone-derived organic tissue. In the preferred embodiment radio frequency energy is applied and the bone or bone-derived organic tissue is in an electrically conductive medium. Further, this invention is a method of electrosurgical treatment of bone or bone-derived organic tissue.

The invention is also of a method of treating bone tissue comprising providing bone segments and placing a bioactive interfacing agent between the bone segments. In the preferred embodiment, the interfacing agent comprises one or more of osteoconductive, osteoinductive, and osteogenic substances or agents. The interfacing agent preferably comprises a hydrophobic, lipophilic carrier past-gel-like material and is activated by electromagnetic energy (preferably radio frequency energy) and/or heat releasing microspheres.

A primary object of the present invention is to provide an in vivo procedure for fusing/welding bone in a fluid medium, such as during endoscopy. More specifically, the present invention provides a means for performing in vivo fusing or welding of bone without the need for supplemental fixation devices. Therefore, an additional primary advantage of the present invention is to provide a means to achieve sufficient joining strength between bone segments such that supplemental fixation devices are not required during the healing process whereby eliminating the sequelae of such devices. The process further provides the primary advantage of the use of a biocompatible interfacing agent that augments the structural weld strength and contains bioactive agents that augment the healing response. Further, the use of electromagnetic energy, and specifically radio frequency, is applied to bone or bone-derived tissue for the first time. This occurs in an electrically conductive medium with the use of an instrument probe. Both the mechanical and biologic environments necessary for bone healing are addressed and augmented in this invention.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTIONS OF THE DRAWINGS

FIG. 1 is an illustration of cancellous and cortical bone comparing major structural morphology. Note the gross structural differences between cancellous bone and cortical bone. This fundamental structural difference has direct implications for the method of bone welding as disclosed.

Figure 2:
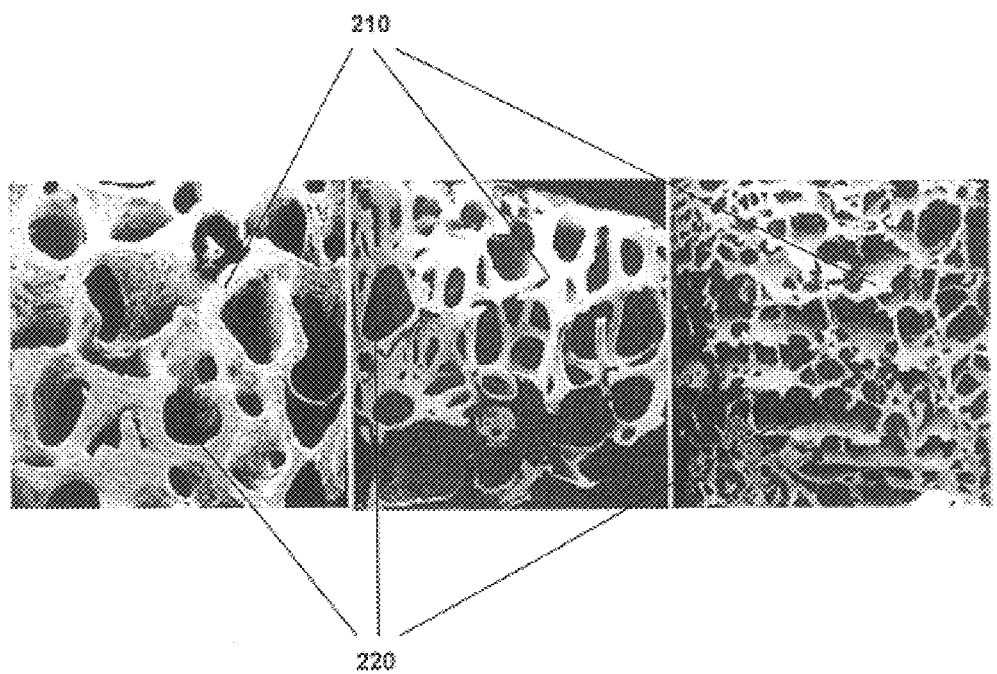

FIG. 2 is a series of electron micrographs depicting the structure of cancellous bone from various anatomic locations. Note the large number of bone spicules 210 available for fusion/welding. Note also the large porous interstices 220 that allow for the interdigitation of the bone-derived composite (biologic interfacing agent) with a significantly large surface area per unit of measure when used with the bone spicules.

Figure 3:
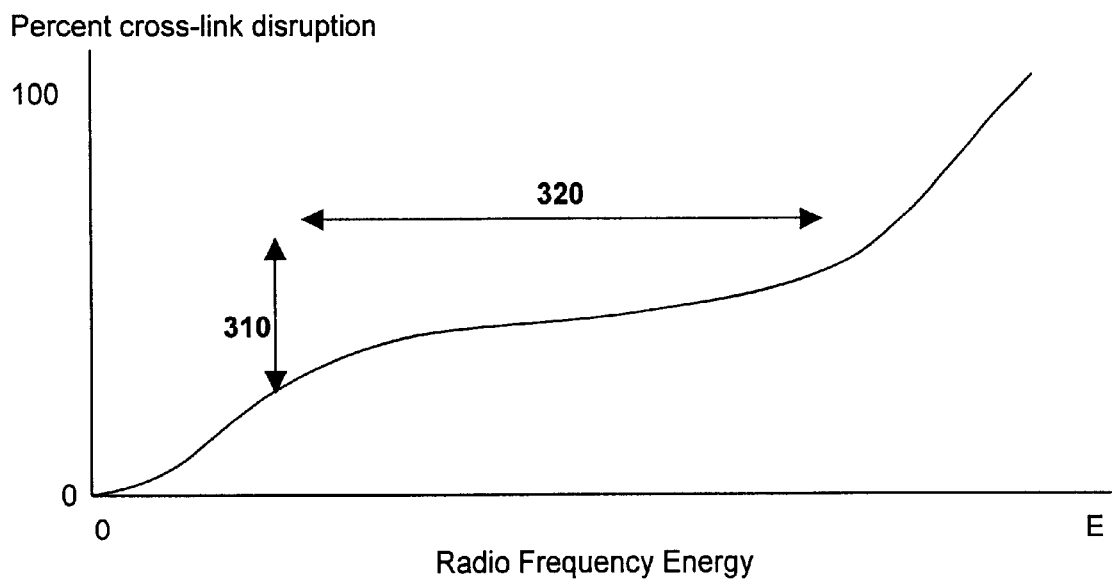

FIG. 3 graphically illustrates the electromagnetic energy absorption structural capacity of bone-derived type-1 collagenous tissue after removal of the inorganic component as described in this invention relative to electromagnetic energy input. A small range of cross-link disruption 310 occurs during a wide range of radio frequency treatment 320 of bone-derived type I collagen relative to level of energy application. This phenomenon allows maintenance of structural integrity during radio frequency energy application.

Figure 4:
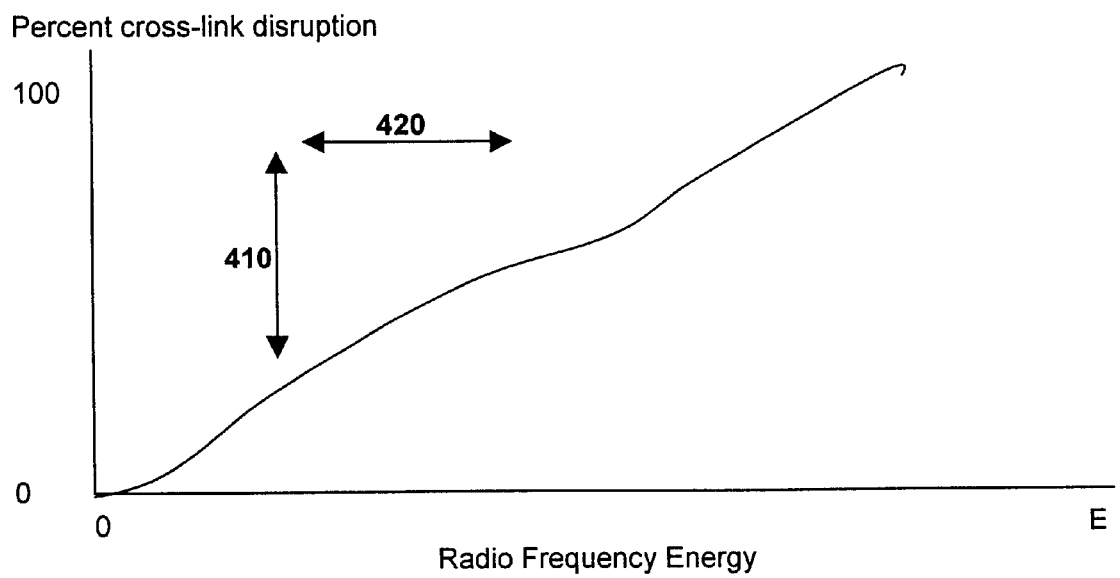

FIG. 4 graphically illustrates the electromagnetic energy absorption structural capacity of soft tissue-derived type-1 collagenous tissue relative to electromagnetic energy input. A large range of cross-link disruption 410 occurs during a small range of radio frequency treatment 420 of soft tissue-derived type-I collagenous tissue. This phenomenon does not allow maintenance of structural integrity during radio frequency energy application.

Figure 5:
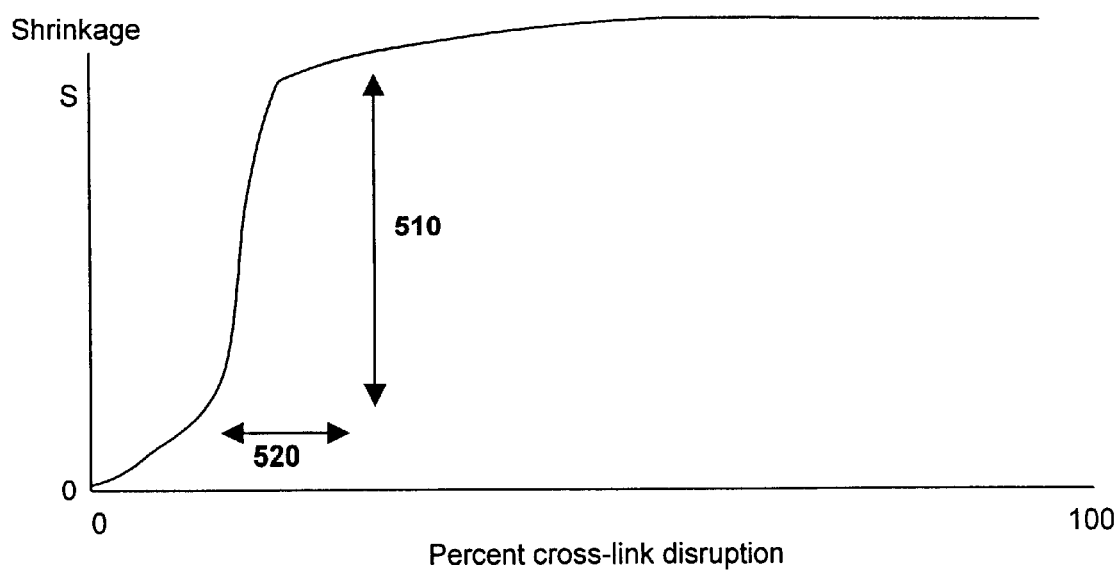

FIG. 5 graphically illustrates the large range of shrinkage 510 per percent cross-link disruption 520 that occurs during radio frequency treatment of bone-derived type I collagen. This phenomenon allows compression to occur at the spicule level (FIG. 2, 210) of the cancellous bone (FIG. 7).

Figure 6:
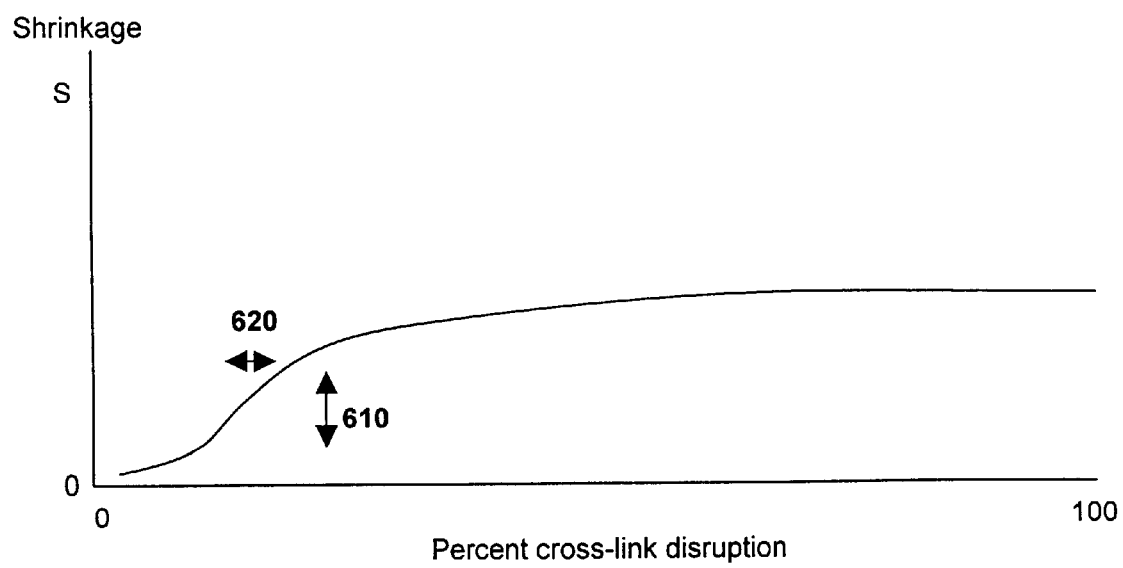

FIG. 6 graphically illustrates the small range of shrinkage 610 per percent cross-link disruption 620 that occurs during radio frequency treatment of soft tissue-derived type-I collagen. This loss of structural integrity obviates the ability to utilize soft tissue-derived collagenous material for the bone fusion/welding process disclosed.

Figure 7:
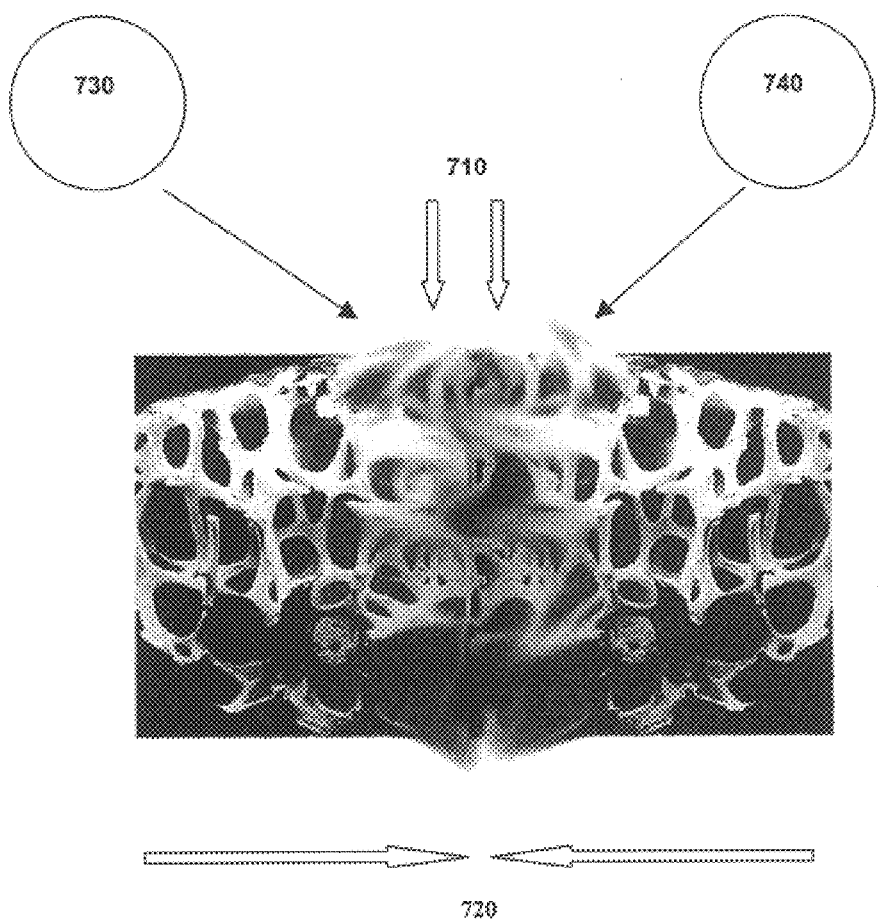

FIG. 7 illustrates electromagnetic energy application to the composite as disclosed. Bone segments are locked together much like the analogy of cement and rebar. When electromagnetic energy 710, such as radio frequency energy, is applied to this construct, the energy is transmitted preferentially within the bioactive interfacing agent inducing shrinkage and coalescence to itself in a three-dimensional pattern that locks the porous recipient bone segments together much like the setting or curing effects of cement or grout reinforced by steel rods or rebar (the cancellous bone spicula and lattice network of the recipient untreated, i.e., undemineralized, bone segments to fuse/weld serves as the "rebar" and the bioactive interfacing agent serves as the "cement" after radio frequency treatment). This figure demonstrates the composite weld at the junction of two recipient bone segments. Initial compression of the segments allows direct apposition and penetration of the interfacing agent. The electromagnetic energy induces further compression at the spicule level 720 through the bone-derived collagen shrinkage while adding the benefits of bone graft derived osteoinduction and osteoconduction. This process does not interfere with healing, rather it augments healing. Additional bioactive agents 730 are added to the hydrophobic lipophilic interfacing agent 740.

DESCRIPTION OF THE PREFERRED EMBODIMENTS (Best Modes for Carrying out the Invention The present invention is directed to the in vivo fusing or welding of bone in a fluid medium. The invention is useful for in vivo procedures in humans and animals. In particular, the process is useful for endoscopy procedures, e.g., arthroscopy or other joint procedures, but is applicable to all clinical uses because a fluid medium generally exists during all in vivo conditions and during all healing processes. In such endoscopy procedures, nicks or other openings are made in the skin and a probe and other instruments, devices, or products are disposed into the body cavity. A camera, or other visualization device, is directed in an opening to view the affected joint, bone, or body cavity.

Two general types of bone exist in the mature organism and are quite similar in all species. Bone is formed based upon the mechanical loads that are applied to the tissue at specific locations by the means of mechanotransduction, i.e., each type is a function of the mechanical environment within which it resides. Cortical bone is the envelope of long bones or cuboid bones and is mainly subject to bending, torsional, and compressive stresses. Structurally, cortical bone consists of dense or compact layers of lamellar bone and woven bone without open spaces or cavities (i.e. non-porous). Cancellous bone is a porous three-dimensional lattice network that is mainly subject to compressive stresses. Cortical bone has four times the mass of cancellous bone yet cancellous bone has eight times the rate of metabolic turnover of cortical bone (cancellous bone is a better source for bone grafting). The porosity of cortical bone is <10% whereas the porosity of cancellous bone is 50–90%. See FIG. 1 and FIG. 2. The inorganic phase of bone is composed principally of calcium phosphate mineral; the organic phase of bone is composed of 90% type I collagen. The material properties of the bone types (energy behavior, strength, energy absorption, ductility, brittleness, viscoelastic behavior, strain rate sensitivity, fatigue properties, and creep behavior) are affected by many variables and these variables can be manipulated for specific treatment purposes. Further, the unique properties and architecture of cancellous bone, i.e. the porosity and the management of compressive stresses, yield a suitable substrate for the fusing/welding process as disclosed below.

Bone that is harvested from a patient to be utilized at another site to assist in bone healing, treatment procedures, and reconstruction is termed "autologous bone graft". Advantages of autologous bone graft include no risk of graft rejection, rapid incorporation, augmentation of healing, and limited harvest site morbidity. Studies have demonstrated that cells from autologous bone graft actually are involved in the fusion mass that occurs during the healing process reinforcing the bioactive role of this procedure (S. E. Gould, et al., "Cellular contribution of bone graft to fusion", *Journal of Orthopaedic Research* 18:920–927 (2000)). Bone graft that is harvested can be manipulated in vitro to then be used in vivo for specific treatments. For example, it can be mechanically modified such as contouring to fit specific defects, morcellized to mold around treatment sites, or physically compressed into a smaller area to augment mechanical and structural properties of the treatment area. Additionally, bone graft can be chemically modified. Preferably, this would be performed in vitro due to possible damage to normal host tissue, but may under certain circumstances be performed in vivo. For example, acid can remove the mineral component of the bone graft and a residual portion of the graft would remain devoid of the rigidity induced by the mineral component. This residual portion retains its bioactive properties and can augment bone healing when utilized in an autologous bone graft fashion (M. Zhang, et al. "Effects of the demineralization process on the osteoinductivity of demineralized bone matrix", *Journal of Periodontol* 68(11):1085–1092 (1997)). Further, this material retains its stimulatory properties even after heating which will be important in the disclosure below (T. Ito, et al., "Sensitivity of osteoinductive activity of demineralized and defatted rat femur to temperature and duration of heating", Clin Orthop 316:267–275 July (1995)). This collagen-based residua retains a structural composition that is malleable and holds a consistency similar to the native cancellous bone of origin. Further, this residua is amenable to modification with electromagnetic energy, such as radio frequency energy. Such processes have not been previously described or disclosed.

Radio frequency energy effect upon soft tissue-derived type I collagen has been well established and the observations continue to grow; however, no data has been previously described for bone-derived collagenous material. Generally raising the temperature of soft tissue-derived collagen via electromagnetic energy can induce modifications in its material properties (energy behavior, strength, energy absorption, ductility, brittleness, viscoelastic behavior, strain rate sensitivity, fatigue properties, and creep behavior). The radio frequency induced behavior of soft tissue-derived type I collagen is affected by many factors including most notably the constitution of it's specific tissue-of-origin (this will be important in the disclosure below). For example, tendon, ligament, and joint capsule collagen, while all soft tissue-derived and primarily type I in nature, demonstrate substantial response differences to electromagnetic and particularly radio frequency energy application. These differences not only lie in the amount of energy that can be absorbed prior to denaturation, but also in the mechanical and viscoelastic properties thereafter. In general, during controlled radio frequency energy application, soft tissue-derived type I collagen can undergo shrinkage and fibril coalescence (M. S. Wall, et al., "Thermal modification of collagen", *Journal of Shoulder and Elbow Surgery* 8:339–344 (1999); M. J. Lopez, et al., "Effects of monopolar radio frequency energy on bovine joint capsular mechanical properties", *Clinical Orthopaedics and Related Research* 374:286–297 (2000); and S. S. Chen, et al., "Heat-induced changes in the mechanic of a collagenous tissue: Isothermal, isotonic shrinkage", *Journal of Biomech Eng* 120:382–388 (1998)). The present invention harnesses the novel and heretofore unknown and untried effects of electromagnetic energy, and specifically radio frequency energy, application upon bone-derived collagen and collagenous material and the benefits thereof in the bone fusing/welding process disclosed below.

Radio frequency energy delivery can be strongly affected by pH, electrolyte concentration, hydration levels of tissue, and tissue impedance. Additionally, weaker radio frequency energy delivery effectors include collagen organization and tissue senescence. Electromagnetic energy, specifically radio frequency, can induce changes by rapidly oscillating electromagnetic fields that cause movement of charged particles within substances and tissue with the resultant molecular motion, activity, and reaction causing heat. Current transmission modes are via ionic or electrolytic solutions and generally follow the path of least resistance, a parameter that describes tissue impedance. Transmission cannot occur to an appreciable level in non-ionic or non-electrolytic environments or in areas with high impedance to such energy currents. In such non-conducting fluid media, radio frequency energy, for example, is dissipated in electromagnetic field emissions similar to radio waves. In the presence of conductive fluid media, soft tissue is rapidly affected by radio frequency energy. The heat-liable collagen cross-links are disrupted and the material undergoes transformation from a highly organized crystalline structure to a more random gel-like material. This process has been termed "Phase Transition" for the collagen derived from soft tissue; changes which are based upon the tissue-of-origin (P. J. Flory, et al., "Phase transitions in collagen and gelatin systems", *Journal of the Am Chem Soc* 80:4836–4845 (1958)).

This process occurs in a different manner with bone-derived collagen, most notably with the resultant material displaying quite different properties from that of soft tissue-derived collagen under similar treatment protocols. Controlled application of radio frequency energy to the residua of cancellous bone graft after removal of the mineral-inorganic component (such as with acid treatment) yields a substance that retains a cohesive network of fibrils that provides structural strength of a much broader nature that soft tissue derived collagen under similar radio frequency treatment protocols. Generally, application of radio frequency energy to soft tissue-derived collagen induces a phase transition including shrinkage and coalescence. The tissue's structural properties decrease with this treatment (A. L. Wallace, et al., "Electrothermal shrinkage reduces laxity but alters creep behavior in a lapine ligament model", *Journal of Shoulder and Elbow Surgery* 10(1):1–6 (2001)) i.e., the soft tissue-derived collagen is less able to withstand tensile loads as well as static and cyclic creep strain. These findings have been quite problematic for clinical use since such mechanical environments are typically required during the healing process in vivo. However, bone-derived collagenous tissue yields a material that can support tensile properties to a much greater degree due to the varied, specific, and unique cross-linking and coalescence properties exhibited in the native and treated structure. Although the specific molecular process have not been clearly elucidated, these properties have been shown to be three to four times as large and are felt to be due to the specific interactions within the native cancellous bone structure prior to harvest and treatment, such as the profile and pattern of bone-derived collagen cross-linking. This phenomenon is generally described in terms of those cross-links that are stable or unstable to the effects of electromagnetic energy application. The unstable cross-links allow denaturation and fibril coalescence while the stable cross-links allow shrinkage that can generate tension. Particularly, the unique bone collagen cross-linking patterns are derived from lysine and hydroxylysine via deamination by lysyl oxidase, which produces an aldehyde amenable to condensation with a lysyl or hydroxylysyl residue of a neighboring collagen molecule. The resulting divalent aldimine and oxo-imine cross-links are incorporated in trivalent hydroxylysyl-pyridinoline and lysyl-pyridinoline cross-links. The mechanical properties of bone and soft tissue (even within soft tissue type) differ substantially even though type I collagen predominates in each tissue type. Other constituent factors impart these differences. The other factors and components that allow for such differences in the material properties before treatment also allow for such differences after treatment. These post-radio frequency treatment mechanical properties of bone-derived collagenous tissue are to be utilized in this bone fusing/welding process.

Electromagnetic energy, and more specifically radio frequency energy, induces disruption of cross-linking between collagen fibers. The degree to which this cross-linking is disrupted depends upon the native tissue-of-origin and is a function that describes the disruption of structural integrity induced by such energy application. Bone-derived collagen responds differently than soft tissue-derived collagen. These properties are displayed in FIGS. 3, 4, 5, and 6. This invention takes advantage of this newly described phenomenon, not only via the natural insulating effects for controlled application (as disclosed below), but also for the variability between patients and treatment conditions. The bone-derived tissue contraction that occurs with radio frequency application is able to generate the internal compression (disclosed below) that bone healing requires at the bone spicule level while also providing the mechanical stability required. If most cross-links were disrupted with such treatment, as is often evident with similar treatment upon soft tissue-derived collagen, no tension could be developed within the bone construct and no compression or mechanical stability could be achieved. This varied disruption of structural integrity is a fundamental difference between electromagnetic energy, and specifically radio frequency energy, application upon soft tissue-derived and bone-derived collagenous tissue and this disclosure has been used for the bone fusing/welding process of the present invention.

Further, radio frequency energy demonstrates no significant effect upon native untreated bone with the energy levels utilized clinically in collagen tissue treatment. The pathway for conductivity retains a very high resistance (tissue impedance) when compared to other tissue types and surrounding fluids. Accordingly, it is, and has been to date, unexpected that radio frequency energy would retain a place in the treatment of bone tissue. The inorganic phase of bone provides a natural insulator against damage to its composition from radio frequency energy and the treatment outlined above occurs only after this phase has been eliminated. This characteristic is due to the nature and manner by which the bound ionic elements reside within the native mineralized bone structure. This phenomenon allows unaltered bone to serve as a natural insulator against collateral damage when utilizing radio frequency energy upon bone tissue or adjacent tissue within the parameters typically utilized. This natural insulation does not occur for example with laser application as the photostimulation will occur in normal bone as well as treated bone, limiting its role for clinical use (e.g. iatrogenic osteonecrosis). As this technique can be utilized to control the application of radio frequency energy to tissue, and particularly to bone tissue, bone welding is now made possible for the clinician.

Briefly, and to this end, if bone fusion/welding is necessary as part of the surgical procedure, a piece of autologous bone is harvested from another part of the body. The harvested bone and/or the joint/recipient bone that is being repaired are treated via methods disclosed below. The harvested bone is preferably treated in vitro and includes the addition of other substances as disclosed below to create an interfacing agent for the fusion/welding process. The joint or receiving bone, because it remains in the host body, must be treated in vivo. Therefore, simple "de-fat" procedures that are biocompatible have been sufficient for the in vivo recipient bone segments. The harvested bone is provided to the affected joint or receiving bone and then two recipient bones are fused/welded in vivo using heating methods and technologies such as but not limited to chemical heating gels, ultrasonic vibration, photonic energy, etc. Based upon the above disclosure, the current preferred embodiment uses radio frequency electromagnetic radiation. Since the procedure occurs in vivo, it occurs in a fluid medium, additionally amenable to endoscopy and electrosurgical procedures.

In the present invention, the harvested bone and/or the recipient bone may be chemically or mechanically treated to remove or alter the mineral matrix and provide a good fusion/welding surface. Because the fusing/welding occurs in a fluid medium and in vivo, any chemical utilized upon the recipient bone in particular must be safe to the human or animal and to the tissues being treated. In the case of acid pre-treatment of bone surfaces, dilution is necessary. Or, other acids or chemical compositions, friendly to the host, may be used such as acetic acid, citric acid, malic acid, or other acids found normally in human ingested foods or endogenously produced by the host organism. Generally, the harvested bone tissue is treated with demineralization procedures as disclosed below; the recipient bone is treated with biocompatible agents to "de-fat" the porous intersticies, such as hydrogen peroxide, evacuating those spaces to accommodate the introduction of the bioactive interfacing agent (i.e. the treat harvested bone material) as disclosed below. The additional step of demineralization of the recipient bone segments may be required in some instances to a limited degree and will become apparent to those skilled in the art.

In the present invention, the new and novel configuration of interface agent is comprised primarily of a biocompatible acid treated bone-derived graft material, a carrier substance that allows use in a fluid environment, a visualization aid, a substance that channels the electromagnetic energy, and an osteinductive/osteoconductive compound or compounds. An example of such a composite would be citric acid, bone graft, hydroxyapetite, and tricalcium phosphate gel. Such configuration provides greater stability of manipulation and of placement in an in vivo fluid medium such as during endoscopy and addresses all the above stated concerns of prior art for the bone fusion/welding procedures. To those skilled in the art, it is quite apparent that other substances, compounds, or agents may be added as needed for specific treatment purposes.

The invention disclosed herein provides a system for bone fusion/welding that utilizes a new set of techniques and biomaterials for safety, biocompatibility, controllability, and healing enhancement purposes. This system encompasses six primary components with particular attention to the preferred embodiment of radio frequency energy application. However, it will be apparent to those skilled in the art that other nuances or variations may apply for other energy sources. First, a visualization aid is required to assist in locating the anatomic region to be treated via endoscopy techniques or via the direct visualization of traditional open procedures. The preferred embodiment utilizes both a dye enhancement process and biomaterials that interface between the bones to be fused/welded that are visually self-evident. To accommodate visualization via standard endoscopy equipment, a new system of endoscopic lenses would be utilized to accurately visualize the area to be treated. Second, an agent within the interfacing agent composite, that is more conducive to radio frequency energy than normal surrounding or untreated tissue or fluids would effectively channel the electromagnetic energy to the fusion/weld site while protecting the normal or untreated tissue or fluids while facilitating the fusion/welding and healing process. This would take advantage of the controllability of radio frequency delivery mechanisms as discussed above and enable a lower energy fusion/welding process more amenable to in vivo applications. This would prevent unintended application of the treatment to normal and unaffected tissue and add additional safety. Third, interfacing agent enhancing materials are comprised of hydrophobic and lipophilic biocompatible components to allow application in a fluid medium since the fluid or the fusion/welding process could generally distribute the substance(s) into unwanted regions or areas. Fourth, interfacing agent enhancement materials also include weak biocompatible acid(s) agent(s) to pre-treat the bone surfaces that are to be united utilizing the electromagnetic energy. This process when used upon the recipient bones creates the thin layer of treatment of the apposed surfaces to facilitate fusion/welding processes. This process when used upon the harvested bone material exposes the organic component to the affects of electromagnetic energy. Fifth, the interfacing agent would typically include additional bioactive agents that would promote bone healing at the site of fusion/welding in addition to the actual fusion/welding process itself. Examples include but are not limited to tricalcium phosphate, hydroxyapetite, or other similar osteoinductive, osteoconductive, or osteogenic compounds, whether naturally occurring, synthetic, or recombinantly produced. Sixth, the by-products of the welding process, if any, will need to be eliminated or disposed with special instrumentation (disclosed below). These techniques should be amenable to in vivo conditions and compatible with the goals of this treatment, specifically to provide provisional fixation that does not require supplemental fixation devices during the healing process without interfering with the natural healing process in a detrimental fashion but in fact to augment the healing process. It should be apparent to one skilled in the art that all of these attributes can be in one single device or a series of complimentary devices, applied in one step or as a series of steps. The attributes of the interfacing agent may be in the form of a solder, gel, or paste, or other biomaterials such as but not limited to a biomaterial wrap, sponge, putty, glue, wedges, shims, mesh, or adhesive products that would be placed around or adjacent to the bone.

The fusing/welding procedure is preferably accomplished by heating bone segments or other joined bones using radio frequency energy. However, it should be obvious to those skilled in the art that electromagnetic energy across the entire spectrum from ultraviolet to infrared is appropriate if tuned to the correct energy density. As discussed above and based upon the above disclosure, the portion of electromagnetic spectrum that is preferred in this application is the region termed radio frequency. Radio frequency energy induces tissue heating by molecular friction, resistive, and/or conductive heating, or other means whereas laser energy induces photostimulation of cellular matter that generates heat. The method and type of energy delivered to the fusion/weld site will generate specific nuances in the methods for fusing bone and particularly in the biosubstances used to interface the apposed bones. In the instance of some radio frequency delivery mechanisms, the energy is applied to tissues through a path of least resistance; that is penetration of heat is a function the tissue impedance to such energy currents. This phenomenon can be exploited by the addition of conducive radio frequency agents as described above to facilitate the heating process and promoting safety. Additionally, the source of radio frequency equipment will include a generator that delivers radio frequency energy at controlled levels and application times. The energy is applied to tissue surfaces with the use of an instrument probe whose composition induces specific current field geometries. This probe may provide application either via local direct tissue contact, local indirect non-tissue contact, or via antennae transmission to a location specified away from the probe tip. The energy can be delivered via multiple modes including but not limited to either a monopolar or bipolar fashion. Further, the specific fluid medium in which the fusion/welding process can occur may be changed in series to address each step of the process as disclosed. Generally, a probe tip configuration must accurately treat the area and dispose of the necessary by-products, if any, of the fusion/welding process. Such instrumentation provides for evacuation of the immediately surrounding fluid near the fusion/welding site. Additionally, electrode configurations are such that electromagnetic energy is "broadcast" over the entire fusion site bathing the overall site in low-density electromagnetic field energy. Secondary probe configurations provide for more concentrated localized flux fields that treat highly specific areas to promote final fixation through higher levels of heating to the specific treatment zone.

Furthermore, in this method of fusing/welding bone under in vivo conditions, and specifically under endoscopic conditions, a defect or fracture that is either created via injury or disease, or via iatrogenic means in the normal course of a specific orthopedic procedure, is contoured to a specified shape and fitted with the bone to which it is to be joined much like the pieces of a puzzle (for example, a cylinder hole-tunnel with a cylinder bone plug compressed into the hole-tunnel or a key hole design). This one-to-one fit allows direct apposition of the bone surfaces to be fused/welded and has the additional benefit of resisting the normal physiologic forces to which the fusion areas are typically initially subject. The two bones to be joined are preferably held together with external pressure or are "pressure-fit" during the fusion/welding process. A compression fit is generated by the bone tissue itself as it is introduced into place with special impacting and delivery instrumentation. The bioactive interfacing substance can assist the compression fit by being configured to swell in the presence of fluids or in the heating process. This compression fit can be augmented by other temporary traditional provisional fixation techniques, if required, such as interference screws, wedges, biodegradable devices, shims, etc. until the weld is complete and then would subsequently be removed at the completion of the procedure. These swelling and fixation components may be combined into the above-described bioactive interfacing agent as a single device or used as complementary devices. Additional bone graft or biomaterial could then be placed into the small defect that has been created by the temporary provisional fixation device as described here and another application of the welding techniques can be performed thereafter.

Based upon the above considerations and in a further descriptive extension of the embodiments, the present invention utilizes autologous bone graft, preferably cancellous in nature but may in some circumstances contain cortical or other autologous bone structures, that is harvested from a patient to be utilized at another site to assist in bone healing, treatment procedures, and reconstructions that require bone fusing/welding. The autologous bone graft is chemically treated as described above to remove the mineral inorganic component of harvested bone while retaining the integrity of the organic component and its bioactive and electromagnetic energy response properties. Typically concentrations between 10% and 25% muriatic (HCl) acid are utilized for 2 to 10 seconds followed by washing with normal saline to remove the acid (the concentration and the type of chemical treatment can vary as necessary to remove the inorganic phase/mineral component of specific bone harvest origins). Hydrogen peroxide may additionally be used for "de-fatting" the harvested bone. Typically 3% hydrogen peroxide solution allows the necessary de-fatting and remains biocompatible. Other decalcification techniques, such as microwave decalcification, EDTA, silver, or other types of acid treatments or sequences of treatments, known to those skilled in the art will become readily apparent as other means to obtain the organic bone-derived tissue that is amenable to radio frequency energy treatment. Further, the addition of compounds or growth factors to this post-treated autologous bone graft material, such as but not limited to hydroxyapetite, osteogenic protein, hormones-like substances, insulin-like growth factors, prostaglandins, chemical mediators, cellular chemotactic substances, transvection vehicles, and other factors to control gene expression, within this bone-derived substance that would promote, stimulate, or induce various healing properties via osteoconductive, osteoinductive, or other methods. Such substances may also be activated by the particular electromagnetic energy source used in the fusion/welding process, such as release from heat-activated microspheres. This complex is additionally combined with a hydrophobic, lipophilic carrier paste-gel-like substance that allows use in a fluid environment. This paste-gel is composed of an ionic substrate that transmits radio frequency energy via its electrolytic properties and is composed specifically for the particular area of treatment and mode of radio frequency use. Materials such as sodium chloride, potassium chloride, or similar ion-liberating based solutions, compounds, or substances are acceptable media and can be combined with specific paste-gel-like carriers. The substrate may exceed the ionic and electrolytic concentration of surrounding tissue and fluid allowing radio frequency energy transmission to be preferential to the substrate and away from normal tissue and surrounding fluids further limiting the potential for collateral damage and unwanted energy application (in addition to the natural insulating effects of natural bone to radio frequency energy), i.e., the path of least resistance or impedance. Additionally, a visualization aid, additive, or dye is included as disclosed above.

This bioactive material as disclosed can then be used as an interfacing agent during bone welding procedures. This new combination of a biocompatible and bioactive components in the interfacing agent demonstrates several benefits during the fusing/welding process as disclosed: 1) directing or channeling the radio frequency energy to the treatment site; 2) utilizing natural untreated bone as an insulator against untoward effects of excess radio frequency energy application; 3) augmenting the healing process due to the residual bioactive components in the material; 4) being amenable to fluid environments (unlike prior art where other agents are water soluble); and 5) participation in the fusion/weld strength providing structural stability and compression between the recipient bone segments as a result of electromagnetic energy application. These attributes follow the fundamental structural and biologic environments necessary for bone healing as described above.

This bioactive interfacing agent is impacted into the porosity of the cancellous bone of the two recipient bone segments to be fused. The recipient bone segments will have been sufficiently prepared in vivo for this introduction by the above disclosed "de-fat" procedures, and at times by demineralization. The two segments are then placed together under a compressive load (amenable for cancellous bone), forcing the bioactive interfacing agent further into the porous interstices of the recipient bone segments. The penetration of the bioactive interfacing agent into the recipient bone porous intersticies is critical to the structural fusion/welding process. At least 2–3 millimeters of penetration into normal "de-fatted" recipient bone segments has been deemed appropriate at each surface of the recipient bone segments. This penetration allows the structural integrity of the mineralized bone spicules to serves as rebar (see disclosure below). To those skilled in the art, it will become apparent that variations in such penetration would exist for specific local and anatomic circumstances. As described above, the recipient bone segments may be a defect that is either created via injury or via iatrogenic means in the normal course of specific orthopedic procedures or bone that is contoured to a specified shape and fitted with the bone to be welded much like the pieces of a puzzle (for example, a cylinder hole-tunnel with a cylinder bone plug compressed in to the hole or a key hole design). This one-to-one fit allows direct apposition of the bone surfaces to be fused/welded. A compression fit is generated by the recipient bone tissue itself and by the interfacing agent as it is introduced into place with special impacting and delivery instrumentation. When radio frequency energy is applied to this construct in vivo, the energy is transmitted preferentially within the bioactive interfacing agent inducing shrinkage and coalescence to itself in a three-dimensional pattern that locks the porous bone segments of the recipient bones together much like the bonding effects of cement or grout reinforced by steel rods or rebar as the cement or gout cures: the cancellous bone spicula and lattice network of the normal "de-fatted" recipient bone segments to fuse/weld serves as the "rebar" and the bioactive interfacing agent, i.e. harvested bone-derived tissue that has been treated to remove the mineral component and impacted into the recipient bone porous intersticies of the "de-fatted" recipient bone, serves as the "cement" after radio frequency energy treatment. See FIG. 7. This interfacing agent during phase transition has become a biologic cement between bone segments that retains biologic bone healing inductive properties. As it contracts, coalesces, and/or shrinks to itself, it further induces compression at the interface of the recipient bone segments to be fused/welded. The radio frequency energy does not significantly affect the recipient bone segments to be fused/welded since the mineral component has not been removed and is thus shielded from the energy effects at the energy levels required. The shrinkage of the bioactive interfacing agent and its composition (namely the harvested bone-derived collagen) causes contraction and develops tension between segments of harvested bone-derived collagenous tissue within itself and therefore this tension is transferred into compression between the recipient bone segments to be welded due to the inter-locking of the "defatted" cancellous portions of the recipient bone segments to the bioactive interfacing agent's contractile nature after electromagnetic energy application. This coalescence creates a single structural unit of the bioactive interfacing agent that induces the weld strength. This phenomenon is possible due to the unique material property response of bone-derived collagenous tissue to radio frequency energy disclosed above. The surface area per cross-sectional area for this weld is very large due to the cancellous porous interstices of the recipient bone segments, and combined with the above considerations of the radio frequency induced changes of bone-derived collagenous tissue of the interfacing agent, the welding strengths are much higher than with the cortical fusing/welding techniques described in prior art. No decay is evident in the fusion/weld since the strength is an inherent construct between the bioactive interfacing agent and the bone segments that has been formed within and between the compressed bone segments that retains structural properties that does not rely upon a single cortical weld surface. In fact, some swelling occurs during the initial normal healing response phase which increases the fusion/weld strength by further augmenting compression at the fusion/weld site of the recipient bone segments. The recipient bone segment-recipient bone segment interface allows a natural healing response due to the apposition of their surfaces in a compression mode without hindering biologic processes. The recipient bone segment-bioactive interfacing agent interface allows joining or union and the development of tension within and between the cancellous lattice networks at the spicule level of the recipient bone segments (the rebar in the cement). Combined, this process induces bone fusing/welding in a fluid (in vivo) environment that creates adequate strength during the natural healing process of bone without disrupting but further augmenting the healing response. This process follows the fundamental mechanical and biologic environments required for bone healing.

Objects and Advantages

Generally, provisional fixation techniques are required in orthopedic treatments to hold tissue (bone sections or fragments) in specific positions until adequate, mature healing responses can be developed by the organism that supercedes the requirement of the provisional fixation initially utilized. The present invention allows bone fusing/welding to become the preferred method of in vivo provisional fixation by providing a means for improved fusion/weld strength and simultaneously allowing a decrease in the requirement of traditional provisional fixation techniques during the treatment procedures. In this manner, the sequelae from the use of such traditional provisional fixation techniques (metal or biologic screws, plates, pins, wires, allograft, etc.) can be decreased and/or eliminated which provides a distinct treatment benefit. Problems such as residual bone defect, exorbitant inflammatory responses, infection, and host rejection are some of the more common problems associated clinically with current provisional fixation devices. The current invention discloses for the first time a true "in vivo provisional fixation technique" that addresses and reconciles both of the fundamental environments required for bone healing (mechanical and biologic).

In vivo bone welding will likely become the preferred method of provisional fixation allowing a decrease in the requirement of traditional provision fixation techniques during the treatment process. The utility of the bioactive interfacing agents combined with highly specific electromagnetic energy means enables the routine use of in vivo bone fusion/welding as a primary mode of fixation for bone segments, both in fracture care and in reconstruction. This includes specific techniques such as biologic fixation of the bone-to-bone interface such as in fracture care, but also in soft tissue-to-bone interface, and other instances like suture anchors or other modes of fixation (such as but not limited to rivets, tacks, staples, screws, shims, etc.) that can be made or contoured from bone material and then welded to other bone segments during specific treatment procedures to provide fixation. Additionally, in situ bone fragments can be fused/welded in vivo to accomplish specific treatment goals by intra-operative manipulation of the bone fragments into appropriate position and followed by bone fusing/welding obviating the requirement for additional provisional fixation techniques necessary to withstand physiologic loads that necessarily occur during the healing process.

A principle object of the invention is a system of in vivo bone fusing/welding that is amenable to the clinical setting. The current invention allows bone segments to be welded in a "flowing" fluid medium utilizing radio frequency energy combined with a bioactive interfacing agent rather than laser and "solders" disclosed in prior art. Configuration of the bioactive agent to be specifically manipulable in the in vivo joint space and retain its effective boundary in a flowing fluid environment provided the link to clinical application and patient care. A fluid medium is important since all biologic processes in vivo including healing occur in a fluid environment. Even further, the current invention addresses the missing component of prior art if fusing/welding of bone is to be used during the fluid flow encountered in endoscopy. Most joint reconstruction procedures involves placement of bone, bioactive agents, devices, and instrumentation in proximity of adjacent articular surfaces, synovium, ligaments, and/or or cartilage attachments. Endoscopy procedures are currently popular due to the lower morbidity, quicker recovery, and lower cost of traditional open procedures. Radio frequency energy is preferred due to its ease of applicability in a fluid environment, affordable market cost and high market equipment availability, lower collateral damage than with traditional laser, safety to operating personnel and patients, and controllability during application. Further, widespread acceptance in clinical practice has been achieved and FDA clearance has been granted for various indications and has led this energy source to dominate clinical practice over the use of other energy sources. A bioactive interfacing agent is required in this setting to increase the weld strength, weld duration, healing rate, and obviate the need for other provisional fixation techniques that retain sequelae. Radio frequency energy and the bioactive interfacing agent as disclosed are uniquely suited for this new in vivo bone fusing/welding process.

Further, electromagnetic energy can damage surrounding normal tissue if not applied in a carefully controlled and limited fashion. In the clinical setting, patient care procedures cannot utilize such energy if significant collateral damage occurs as a procedure sequelae. Laser energy as a form of electromagnetic energy can be directed to the area of application by utilizing a specific light absorbing dye placed at the application site to aid in limiting collateral damage. This interaction is dependent upon the wavelength of the laser energy where specific dyes channel specific laser energy to induce photostimulation of tissue that induces heat. This technique provides a means to localize the energy necessary for the specific treatment purposes. Unfortunately, water absorbs laser light energy as well and since biologic tissues are composed mainly of water, difficulty in preventing collateral damage exists with laser energy despite attempts at localization with light absorbing dyes. During endoscopy procedures, the treatment area is filled with fluid and often continually renewed (flow) that also would absorb energy. Other factors can be manipulated to decrease laser collateral damage such as altering the power density, spot size, and application mode and time. These techniques however rely upon gross tissue examination to determine effects without a natural means of avoiding collateral damage. The present invention provides a bioactive interfacing agent that acts to channel the electromagnetic energy to the agent itself and at the same time benefiting from the natural insulating affects of radio frequency energy upon untreated bone, thereby minimize collateral tissue damage.

To reiterate, the present invention solves certain problems with prior art in addition to the distinction between the previous prior art in vitro procedures and the current in vivo procedures as disclosed, as follows:

Solder Versus Biologic Interfacing Agent.

Prior art indicates that "there does not appear to be a distinct advantage to using the . . . paste procedure" (U.S. Pat. No. 5,498,259). This is easily understood in reviewing such soldering techniques. The soldering paste process is not materially involved in the welding and fixation process and does not induce structural or mechanical rigidity itself (like the cement and rebar analogy above). In this manner, these soldering techniques have been used solely to direct the laser electromagnetic energy to the bone fusion/weld site. Put simply, the paste or solder is an attempt to localize and direct the laser energy. The tissue is heated to create a fusion/weld in the area of the dye relying upon the heated bone segments themselves to fuse rather than relying upon the interfacing agent to become the fusion agent until natural healing occurs.

Water-Soluble Paste.

Prior art has disclosed a paste that is water soluble (albumin or water based) and not amenable to use in vivo in a fluid or fluid-flow environment. Prior art is "an in vitro experiment" that describes "an in vitro pre-provisional fixation technique".

Type of Bone Welded.

Prior art has disclosed a sub-optimal "cortical spot-welding process" rather than a "cancellous continuous-welding process" as described in the present invention. The advantage of the current invention is the creation of a higher surface area of fused/welded cancellous bone, which creates higher fusion/welding strengths per unit area, eliminating the strength decay with time observed in prior art.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of fusing or welding bone in vivo and in a fluid medium, the method comprising the steps of:

harvesting a piece of autologous implant bone;

treating one or more bones selected from the group consisting of the implant bone and a receiving bone to expose organic component;

treating one or more bones selected from the group consisting of the implant bone and the receiving bone by de-fatting;

combining the implant bone with other compounds to create an interfacing agent;

adding the interfacing agent between receiving bone segments to be fused or welded; and fusing or welding in vivo, in a fluid medium, utilizing electromagnetic energy.

2. The method of claim 1 wherein the piece of autologous bone and receiving bone segments comprise cancellous bone.

3. The method of claim 1 wherein in the fusing or welding step, electromagnetic energy is applied to bone or bone-derived organic tissue to achieve tissue changes.

4. The method of claim 3 wherein in the fusing or welding step, radio frequency energy is applied to bone or bone-derived organic tissue to achieve tissue changes.

5. The method of claim 1 additionally comprising one or more steps from the group consisting of chemically and mechanically treating bone or bone-derived tissue to alter mineral matrix and to de-fat and thereby provide a good fusing or welding surface.

6. The method of claim 5 wherein the chemically treating step comprises treating the bone or bone-derived tissue with acid.

7. The method of claim 5 wherein the mechanically treating step comprises treating the bone or bone-derived tissue to conform it to a shape of another bone.

8. The method of claim 1 additionally comprising the step of compressing the bone segments and interfacing agent during the fusing or welding step.

9. The method of claim 8 wherein the compressing step ceases after the fusing or welding step is completed.

10. The method of claim 1 wherein the fusing or welding step comprises fusing or welding by one or more means selected from the group consisting of heating and electromagnetic energy means.

11. The method of claim 10 wherein the fusing or welding step comprises employing a means selected from the group consisting of lasers and radio frequency generators.

12. The method of claim 11 wherein the fusing or welding step comprises employing an electromagnetic instrument probe with broadcast emission capability and scaled reflector geometry of active electrode design to generate radio frequency energy.

13. The method of claim 12 wherein the fusing or welding step occurs in an electrically conductive medium.

14. The method of claim 1 additionally comprising the step of repeating the harvesting and fusing or welding steps with a second piece of bone in a place previously occupied by a temporary provisional fixation device.

15. The method of claim 1 additionally comprising the step of introducing prior to the fusing or welding step a hydrophobic, lipophilic carrier paste-gel, interfacing agent.

16. The method of claim 15 wherein the introducing step comprises impacting the paste-gel interfacing agent complex into porosity of a bone.

17. The method of claim 15 wherein the introducing step comprises impacting the paste-gel interfacing agent into both the implant bone and the receiving bone.

18. The method of claim 15 wherein in the fusing or welding step the paste-gel operates to direct radio frequency energy into portions of bone to be fused or welded together.

19. The method of claim 18 wherein in the fusing or welding step the paste-gel additionally operates to insulate against the radio frequency energy portions of bone other than the portions to be fused or welded together.

20. The method of claim 1 wherein the interfacing agent comprises one or more components selected from the group consisting of osteoconductive, osteoinductive, and osteogenic components designed to augment bone healing.

21. The method of claim 20 wherein the one or more components are activated, released, or induced by the application of electromagnetic energy.

22. The method of claim 1 additionally comprising the step of depositing a visualization aid.

23. The method of claim 22 wherein the visualization aid comprises a dye.

24. A fused or welded bone structure prepared by the method of any of the preceding claims.

* * * * *